(12) United States Patent
Campbell

(10) Patent No.: US 9,778,118 B2
(45) Date of Patent: Oct. 3, 2017

(54) BOLT SENSOR ASSEMBLY

(71) Applicant: AKTIEBOLAGET SKF, Göteborg (SE)

(72) Inventor: Andrew Campbell, East Kilbride (GB)

(73) Assignee: AKTIEBOLAGET SKF, Gothenburg (SE)

( * ) Notice: Subject to any disclaimer, the term of this patent is extended or adjusted under 35 U.S.C. 154(b) by 0 days.

(21) Appl. No.: 15/036,624

(22) PCT Filed: Nov. 17, 2014

(86) PCT No.: PCT/EP2014/074737
§ 371 (c)(1),
(2) Date: May 13, 2016

(87) PCT Pub. No.: WO2015/071453
PCT Pub. Date: May 21, 2015

(65) Prior Publication Data
US 2016/0299016 A1 Oct. 13, 2016

(30) Foreign Application Priority Data
Nov. 18, 2013 (GB) .................... 1320282.5

(51) Int. Cl.
*F16B 31/02* (2006.01)
*G01L 1/22* (2006.01)
*G01L 5/00* (2006.01)
*G01H 1/00* (2006.01)
*G01N 25/00* (2006.01)
*G01N 29/14* (2006.01)
*F16C 19/52* (2006.01)

(52) U.S. Cl.
CPC ............... *G01L 1/22* (2013.01); *G01H 1/00* (2013.01); *G01L 5/0004* (2013.01); *G01N 25/00* (2013.01); *G01N 29/14* (2013.01); *F16C 19/522* (2013.01); *F16C 2360/31* (2013.01)

(58) Field of Classification Search
CPC ........... G01L 1/22; G01L 5/0004; G01H 1/00; G01N 25/00; G01N 29/14; F16C 19/522
USPC .................................................. 73/760, 761
See application file for complete search history.

(56) References Cited

U.S. PATENT DOCUMENTS 5,343,759 A * 9/1994 Hesthamar .............. G01L 5/243
73/761
5,483,842 A 1/1996 Foreman
(Continued)

FOREIGN PATENT DOCUMENTS

CH 706531 B1 11/2013
JP 2003112343 A 4/2003

*Primary Examiner* — Max Noori
(74) *Attorney, Agent, or Firm* — Bryan Peckjian; SKF USA Inc. Patent Dept.

(57) ABSTRACT

A bolt sensor assembly provides a body adapted for insertion into a hole in a component, the body having a first end and a second end, and a longitudinal axis extending therebetween. The first end includes an attachment means for attachment of the bolt sensor assembly to the component, and the second end mounts a sensor element, such as a strain gauge element. The sensor element is movable with respect to the body in the direction of the longitudinal axis of the body and the sensor element is constrained against rotation about the longitudinal axis with respect to the body.

19 Claims, 11 Drawing Sheets

(56) References Cited

U.S. PATENT DOCUMENTS

| | | | | |
|---|---|---|---|---|
| 5,970,798 A | * | 10/1999 | Gleman | G01L 5/246 |
| | | | | 73/761 |
| 2005/0056595 A1 | * | 3/2005 | Reamsnyder | B01D 35/143 |
| | | | | 210/741 |
| 2006/0096109 A1 | * | 5/2006 | Corghi | G01D 11/30 |
| | | | | 33/520 |
| 2013/0319551 A1 | * | 12/2013 | Dohi | F16K 31/1221 |
| | | | | 137/551 |
| 2016/0177982 A1 | * | 6/2016 | Kobayashi | F15B 15/2861 |
| | | | | 92/5 R |

* cited by examiner

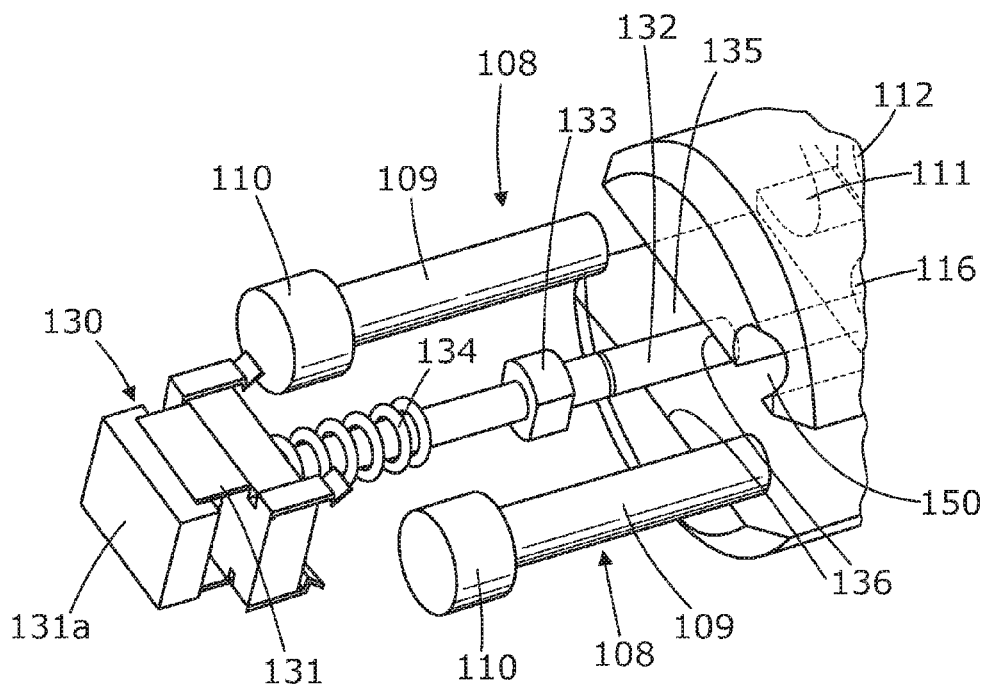
Figure 12
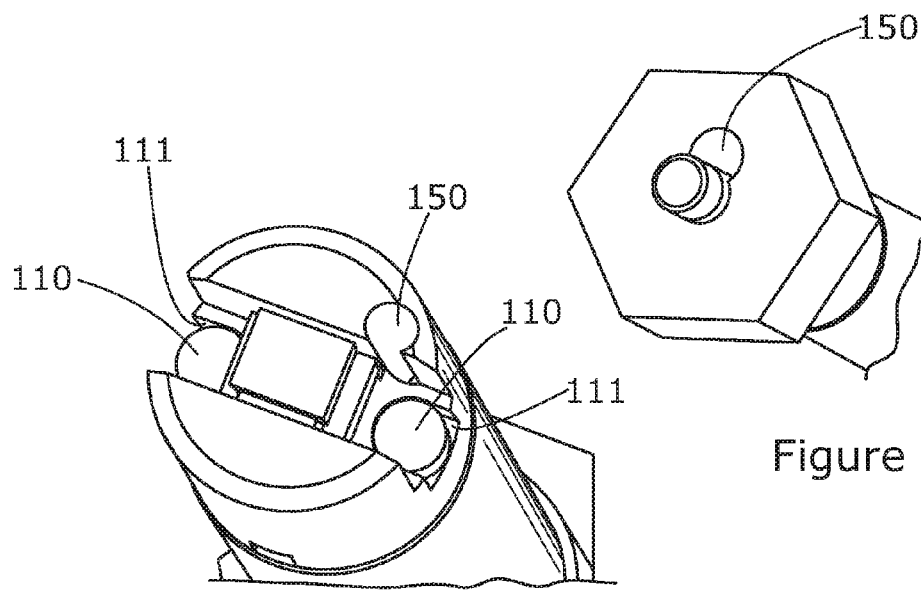
Figure 13a
Figure 13b

BOLT SENSOR ASSEMBLY

CROSS-REFERENCE

This application is the U.S. National Stage of International Application No. PCT/EP2014/074737 filed on Nov. 17, 2014, which claims the benefit of priority from Great Britain Patent Application No. 1320282.5 filed on Nov. 18, 2013, the contents of which are both herein incorporated by reference in their entirety.

FIELD OF THE INVENTION

The present invention relates to mounting of sensor elements, and in particular to sensor elements mountable in a threaded hole.

BACKGROUND OF THE INVENTION

In certain machines it is desirable to be able to measure the load on internal components of the machine. For example, in a wind turbine it is desirable to be able to measure the load on certain bearings.

Many different load measurement devices are available, but often at least a certain amount of disassembly of the wind turbine is required in order to gain access to the bearing.

One possibility for mounting a sensor to measure a load on a bearing is to drill a hole through a part of the component in which the bearing is housed and mount a sensor in that hole. Alternatively, a hole that is present in the component may provide a suitable location to mount a sensor, for example a hole that receives a bolt which is used to remove the bearing from the component may be used.

Strain gauge sensors which can be mounted in holes are well known.

One such strain gauge is described in U.S. Pat. No. 2,873,341. This strain gauge comprises a bolt having a central bore in which is mounted an epoxy core with a resistance wire is embedded therein.

The bolt strain gauge described in U.S. Pat. No. 2,873,341 has the strain measuring element in the centre of the bolt, which is not ideal for measuring strain in a component situated at the end of the bolt.

A more suitable form of strain sensor is a friction strain sensor. Such strain sensors are used in many applications. Such friction strain gauges must be pre-loaded to a certain extent in order to function. Furthermore, friction strain gauges are very sensitive to damage, for example when subject to shear forces. Friction strain gauges are described in general terms in GB 2,367,628.

There seems to be room for improvement.

SUMMARY OF THE INVENTION

According to a first aspect of the invention there is provided a bolt sensor assembly comprising a body adapted for insertion into a hole in a component. The body has a first end and a second end, and a longitudinal axis extending therebetween, wherein the first end includes an attachment means for attachment of the bolt sensor assembly to the component. The second end mounts a sensor element and the sensor element is movable with respect to the body in the direction of the longitudinal axis of the body. The sensor element is further constrained against rotation about the longitudinal axis with respect to the body.

The body is preferably rotatable about the longitudinal axis to engage and disengage the body from the hole. The body may include a threaded portion for engagement with a correspondingly threaded portion of the hole.

Suitably at least a part of the body comprises the second end and the hole are provided with cooperating elements which prevent relative rotation therebetween, and wherein the sensor element is biased to project from said second end of the body. The attachment means then may comprise a collar that is slidably mounted on the body or the attachment means may be mounted on the body for relative rotation therebetween. Suitably a biasing element may be comprised located between the body and the attachment means, the biasing element configured to urge the body and the attachment means in opposite directions along the longitudinal axis. The sensor element may also be comprised in a sensor assembly, which assembly is mounted at the second end of the body, the assembly comprising a base including an opening in which the sensor element is slidably mounted, a reaction member and a biasing means situated between the sensor element and the reaction member. The sensor assembly may further include a mount to which the sensor element is attached and wherein the biasing mean is situated between the mount and the reaction member.

The sensor element may be movable between a first position and a second position. In the first position the sensor element lying behind the second end of the body and in the second position at least a part of the sensor element lying proud of the second end of the body. The bolt sensor assembly may further comprise an actuator adapted to move the sensor element between the first and second positions. The body may include a bore and the actuator then acts on the sensor element through the bore. The sensor element may be mounted on a shaft, and the actuator then engages the shaft. The bolt sensor assembly may further comprise biasing means arranged to exert a force on the sensor element biasing it into the second position. The end of the body in which the sensor element mounted may be configured such that the sensor element is constrained against rotation with respect to the body about the longitudinal axis. The second end of the body may comprise a cap removably attachable to the remainder of the body, the sensor element is then mounted in the cap.

Suitably the sensor element is one or more of an acoustic emission sensor, a vibration sensor, a strain gauge sensor, a friction strain gauge sensor, and a temperature sensor.

According to a second aspect of the invention there is provided a friction strain gauge sensor comprising a body adapted for insertion into a hole in a component, the body having a first end and a second end, and a longitudinal axis extending therebetween, wherein the first end includes an attachment means for attachment of the sensor to the component, wherein the second end mounts a friction strain gauge element and wherein the friction strain gauge element is movable with respect to the body in the direction of the longitudinal axis of the body and wherein the friction strain gauge element is constrained against rotation about the longitudinal axis with respect to the body.

Preferably, at least a part of the body is rotatable about the longitudinal axis to engage and disengage the body from the hole.

The body may include a threaded portion for engagement with a correspondingly threaded portion of the hole.

The body may include a hollow portion, preferably extending from one of the first and second ends.

Advantageously, at least a part of the body comprising the second end and the hole are provided with cooperating elements which prevent relative rotation therebetween, such as a recess and a protrusion engaging the recess. Part of the body may include a rib and the hole may include a recess for receiving the rib.

Preferably the friction strain sensor element is biased to project from said second end of the body.

The attachment means may be slidably mounted on the body and may comprise a collar that is slidably mounted on the body.

The attachment means may be mounted on the body for relative rotation therebetween. The attachment means may comprise a threaded portion for engaging a correspondingly threaded portion of the hole, and the threaded portion may be part of the collar.

The friction strain gauge sensor may further comprise a biasing element located between the body and the attachment means, the biasing element configured to urge the body and the attachment means in opposite directions along the longitudinal axis. The biasing element may be a spring, such as a coil spring.

The body may include a shaft portion of reduced diameter, the biasing element and the attachment means being mounted on the shaft portion.

The body may include an attachment means retaining portion, the retaining portion limiting movement of the attachment means relative to the body.

The friction strain sensor element may be comprised in a friction strain sensor assembly, which assembly is mounted at the second end of the body, the assembly comprising a base including an opening in which the friction strain sensor element is slidably mounted, a reaction member and a biasing means situated between the friction strain sensor element and the reaction member.

The friction strain sensor assembly may further include arms configured for engagement with recesses formed in an inner wall of the body. The arms may be printed circuit boards. The arms may be attached to the base, for example by brackets.

Preferably, the friction strain sensor assembly further includes a mount to which the friction strain sensor element is attached and wherein the biasing means is situated between the mount and the reaction member.

Advantageously, the base is mounted on pins which are slidingly engaged with holes in reaction member. Biasing elements may be provided between the reaction member and the base to urge the base in the longitudinal direction of the body and away from the reaction member. The biasing means may be springs mounted on the pins.

The reaction member is preferably a bridge extending across a hollow portion of the body.

Advantageously, the friction strain sensor element is movable between a first position and a second position, in the first position the friction strain sensor element lying behind the second end of the body and in the second position at least a part of the friction strain sensor element lying proud of the second end of the body, the sensor further comprising an actuator adapted to move the friction strain sensor element between the first and second positions.

The body may include a bore and the actuator may act on the friction strain sensor element through the bore.

Preferably, the friction strain sensor element is mounted on a shaft, and the actuator engages the shaft. The shaft may comprise a collar, the collar configured to constrain the shaft against rotation.

The friction strain gauge may further comprise biasing means arranged to exert a force on the friction strain sensor element biasing it into the second position.

The end of the body in which the friction strain sensor element is mounted may be configured such that the friction strain sensor element is constrained against rotation with respect to the body about the longitudinal axis.

The second end of the body may comprise a cap removably attachable to the remainder of the body, the friction strain sensor element mounted in the cap.

The second end of the body is provided with a seal. The seal may be an O-ring seal. The purpose of the seal is to prevent ingress of contaminants to the area of the friction strain sensor element.

The friction strain gauge sensor may mount other sensors such as, but not limited to, acoustic emission sensors, vibration sensors, temperature sensors.

A second aspect of the invention provides a friction strain gauge sensor according to the first aspect of the invention mounted in a hole in a first component, and the friction strain gauge sensor element engaging a second component.

Other preferred features of the invention can be found in the detailed description of the preferred embodiments.

BRIEF DESCRIPTION OF THE DRAWINGS

In the Drawings, which illustrate preferred embodiments of the bolt strain sensors according to the invention:

FIG. 12 is a detail view of one end of the bolt sensor illustrated in FIG. 10; and FIGS. 13*a* and 13*b* show schematic end views of the bolt sensor illustrated in FIG. 10.

DETAILED DESCRIPTION

Referring now to FIGS. 1 to 4, there is shown a bolt sensor 1 comprising a bolt member 2, and a sensor housing 10.

Figure 4:
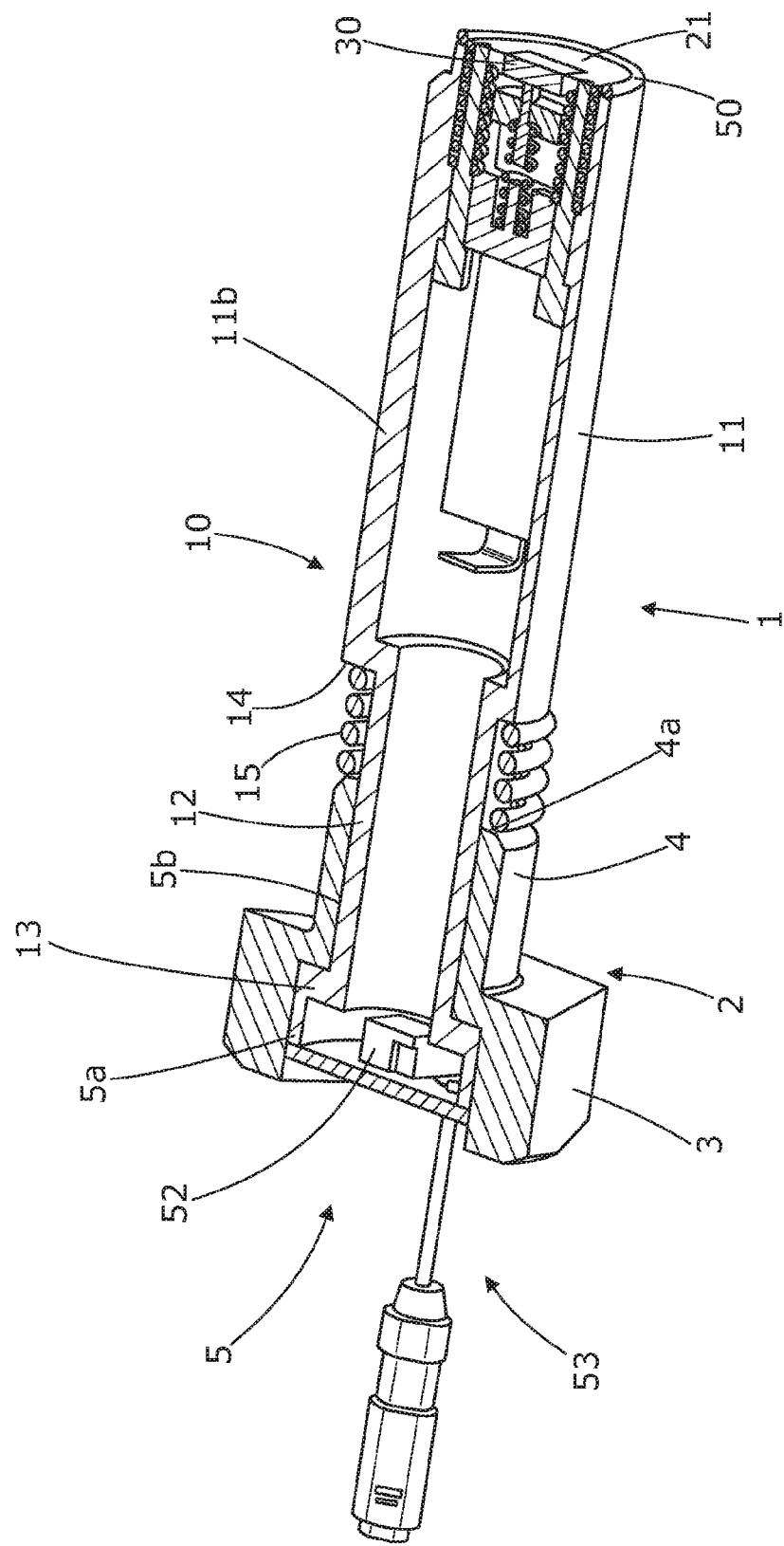
FIG. 4 is a cross-sectional schematic representation of the bolt sensor illustrated in FIG. 1.
Figure 5:
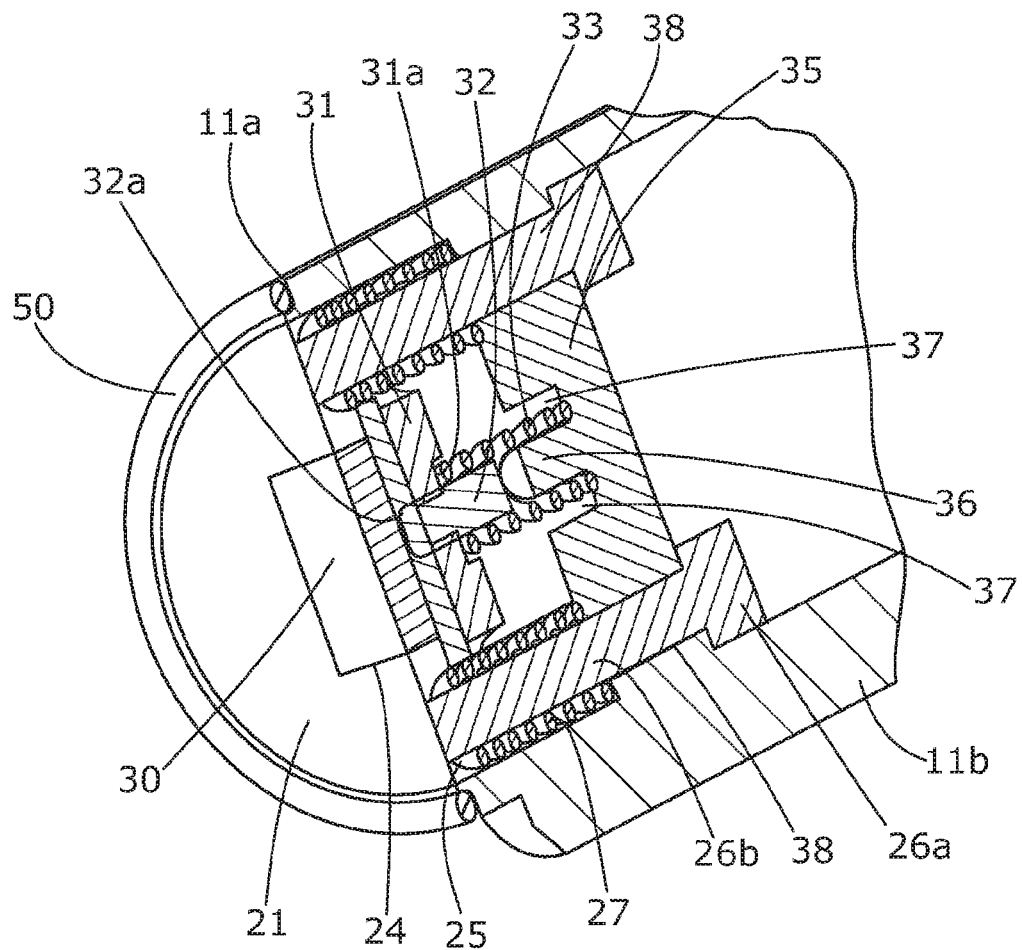
FIG. 5 is a detail view of an end of the bolt sensor illustrated in FIG. 1.

The bolt member 2 includes a hexagonal head 3 and a threaded collar 4. Referring in particular to FIG. 4, it can be seen that a bore 5 extends axially through the bolt member 2, the bore 5 providing two bore sections 5*a* and 5*b*, each of a different diameter.

The sensor housing 10 comprises a hollow portion 11, a shaft portion 12 and a head 13. The shaft portion 12 is of smaller diameter than the hollow portion 11 providing a radially extending rim where the hollow portion 11 meets the shaft portion 12. The head 13 is attached to the end of the shaft portion 12 after the bolt member 2 has been mounted on the shaft portion 12.

A spring 15 is also mounted on the shaft portion 12, between the bolt member 2 and the hollow portion 11. One end of the spring 15 abuts the rim 14. The other end of the spring 15 is engaged by the end face 4a of the threaded collar 4.

The shaft portion 12 passes through and is slidably mounted in the bore section 5b, with the head 13 being located in the bore section 5a. The spring 15 therefore urges the sensor housing away from the bolt member 2, the extent of relative movement between the two components being limited by the head 13 situated in the first bore section 5a.

By mounting the bolt member 2 and the spring 15 on the shaft portion 12, as the bolt member is tightened the spring exerts a force on the housing 10. The head 13 retains the housing 10 in the bolt member 2.

Figure 1:
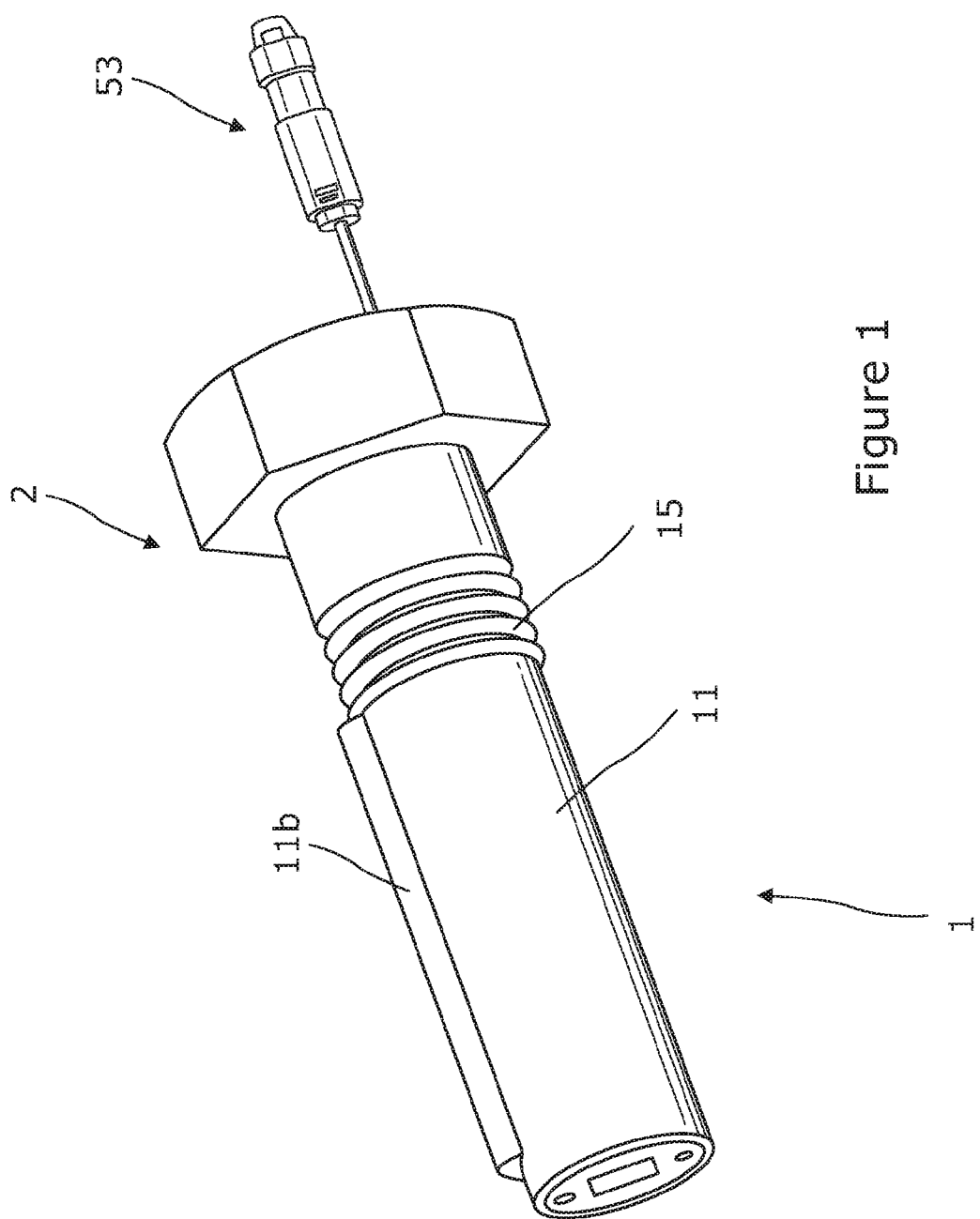
FIG. 1 is a schematic representation of a bolt sensor according to a first embodiment of the invention.
Figure 2:
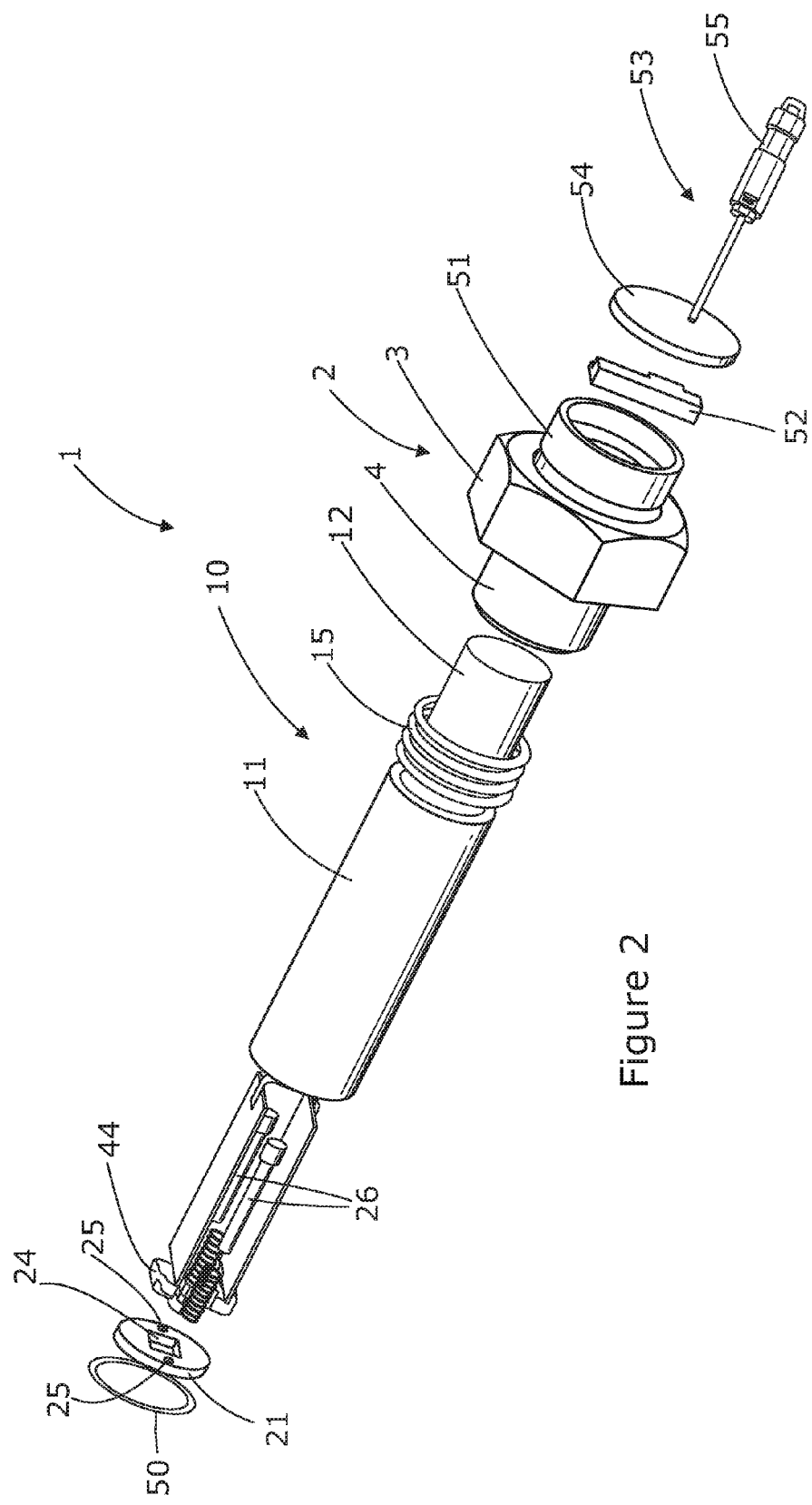
FIG. 2 is an exploded view of the bolt sensor illustrated in FIG. 1.
Figure 3:
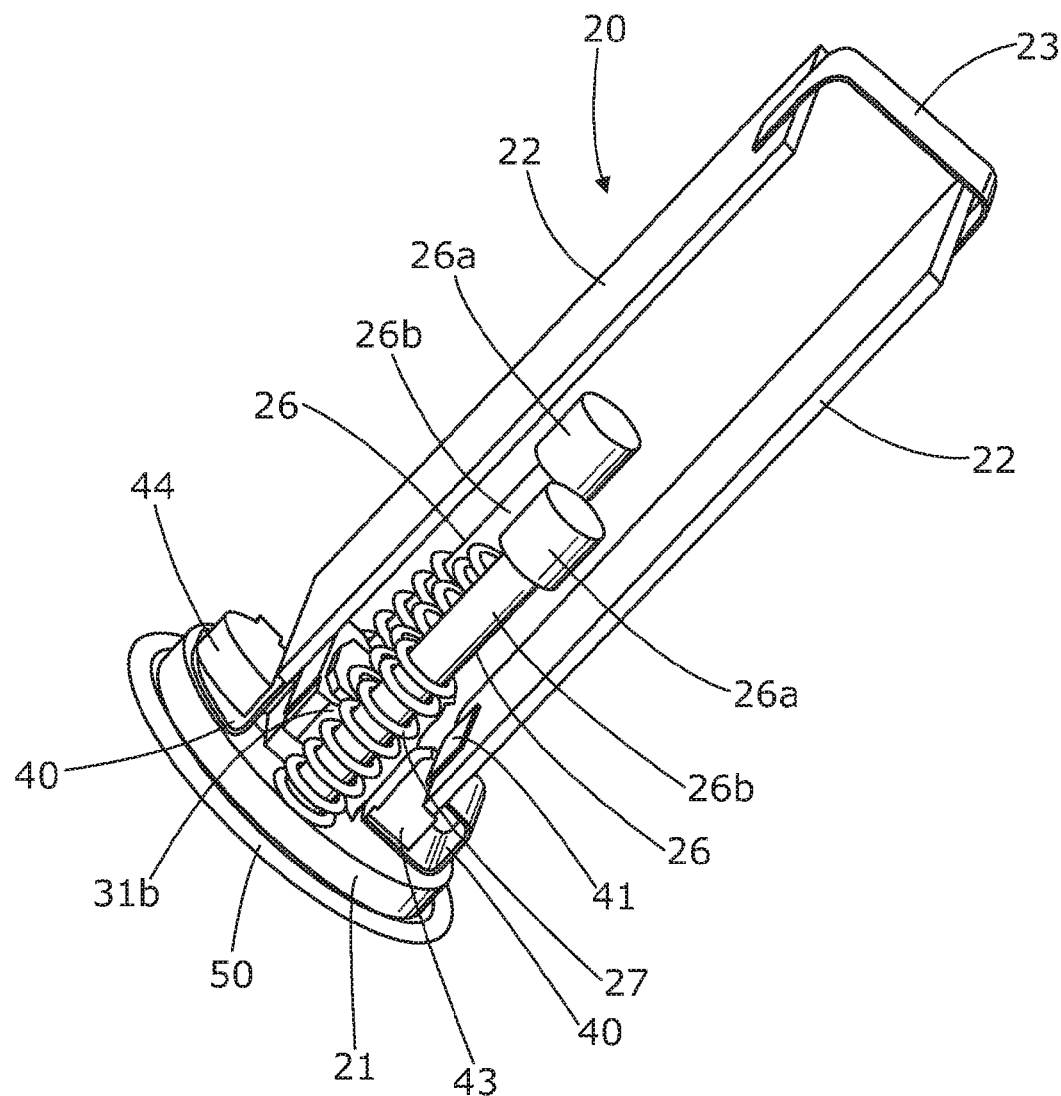
FIG. 3 is a schematic representation of a component of the bolt sensor illustrated in FIGS. 1 and 2.

FIGS. 2 and 3 illustrate a sensor assembly 20, such as a friction strain gauge assembly, comprising a base 21, which is circular in the example, and extending from the base 21 a pair of arms 22 connected together at their ends distal from the base by a connector element 23. The arms 22 are printed circuit boards are connected to the base plate 40 by brackets 40 each including a tab 41 which attaches to one of the arms. One of the brackets 40 may suitably mount a vibration and temperature sensor 43 and the other may mount an AE sensor 44.

The base 21 includes an aperture 24, which is rectangular in the illustrated example, and which is configured to receive the sensor element 30, such as a friction strain gauge, strain gauge, vibration or other type of sensor, as will be described in greater detail below. Two small holes 25 are situated to either side of the aperture 24. The holes 25 each receive a pin 26. The pins 26 each comprise a pin head 26a and a pin shaft 26b. The end of the pin shaft 26b distal from the pin head 26a sits in one of the holes 25. In the present example, the holes 25 and the ends of the pin shafts 26b are provided with corresponding threads to secure the pins 26 to the base 21.

A spring 27 is mounted on the pin shaft 26b. The function of the spring will be described in greater detail below with reference to FIGS. 4, 5, 9 and 9a.

The friction strain sensor element 30 forms part of the friction strain sensor assembly 20. The friction strain sensor assembly includes a plate 31 which mounts a pin 32, the pin 32 fixed to the plate 31, a spring 33 and a bridge 35 extending from one side of the hollow portion 11 to the other. The bridge 35 includes holes 38 through which the pin shafts 26b pass. The pin shafts 26b may slide in the holes 38, the pin heads 26a providing an end stop to movement of the pins 26 and hence the base 21.

The underside of the bridge 35 comprises a central spigot 36, with recesses 37 to either side. One end of the spring 33 sits in the recesses 37. The other end of the spring 33 engages with the plate 31, sitting in an annular recess 31a and receiving the pin 32. The end 32a of the pin 32 is attached to the friction strain sensor element 30.

The friction strain sensor assembly 20 is inserted into the hollow portion 11 of the sensor housing 10 without the cross-member 23 in place. The arms 22 engage in slots 39 in the inner wall of hollow portion 11 and may slide therein. The cross-member 23 is attached to the arms 22, by soldering from example, post insertion of the friction strain sensor assembly 20 into the hollow portion. Cross-member 23 in some embodiments may be omitted. The mounting of arms 22 in slots 39 assists in resisting rotational forces experienced by the base plate 21.

The base 21 is slidable into and out of the hollow portion 11, this securing the friction strain sensor assembly 20 in the hollow portion 11, sliding of the base 21 out of the hollow portion 11 being constrained by the pin heads 26a coming into engagement with the surface of the bridge 35.

The lower edge of the hollow portion 11 is provided with a rebate 11a in which a seal 50 sits. The hollow portion also includes on its outer surface a protrusion, which in the present example is a rib 11b.

Figure 6:
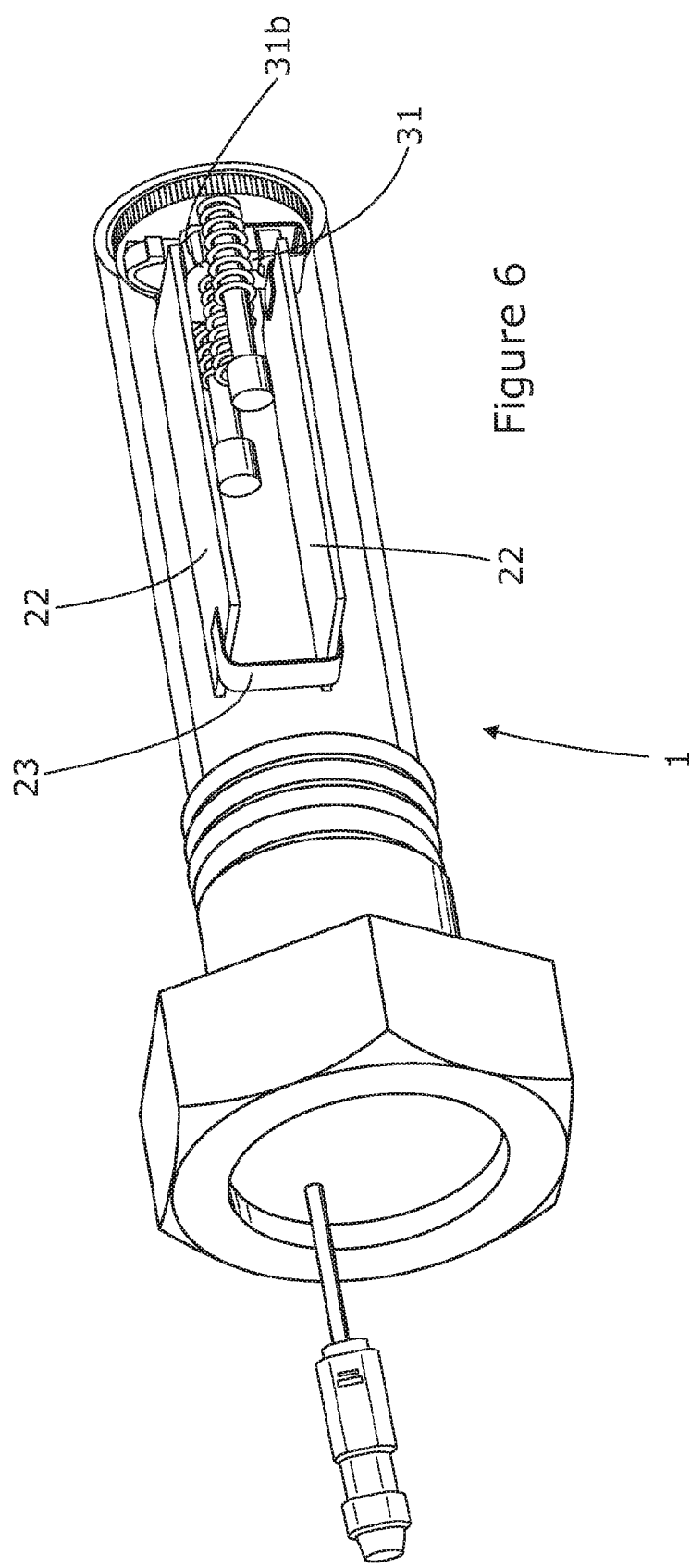
FIG. 6 is a schematic representation of the bolt sensor illustrated in FIG. 1 showing the internal components.

Referring to FIGS. 3 and 6 in particular, it can be seen that the plate 31 includes curved recesses 31b into which the springs 27 extend.

Figure 7:
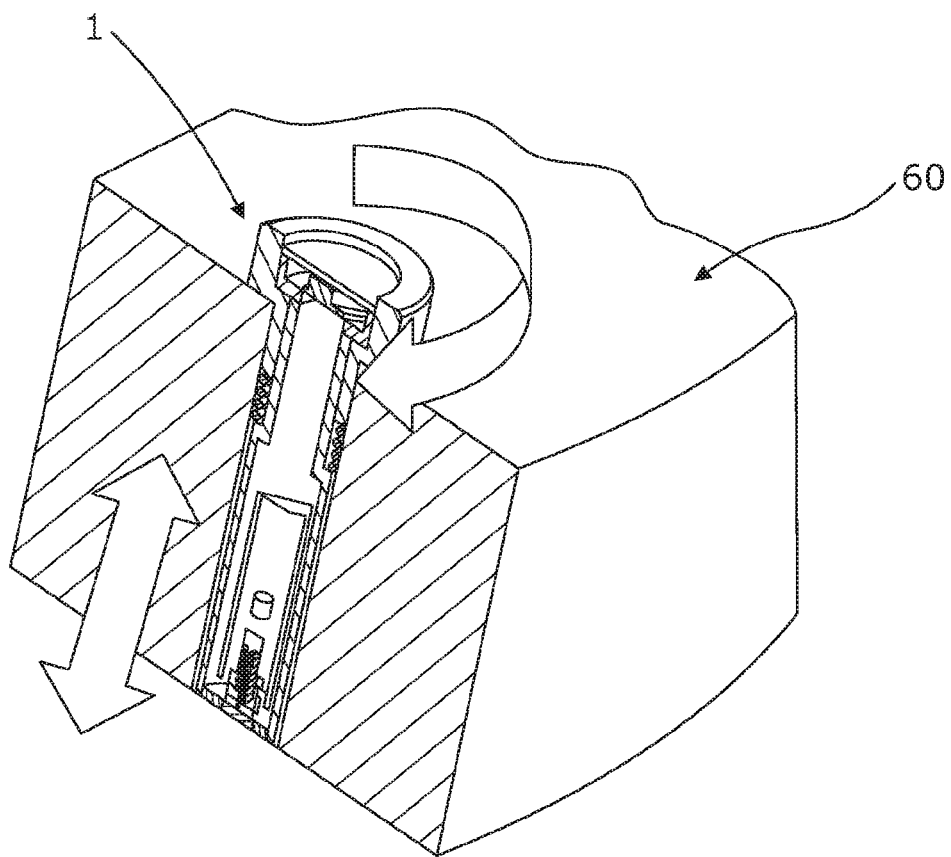
FIG. 7 is an illustration of the bolt sensor shown in FIG. 1 mounted in a housing.
Figure 8:
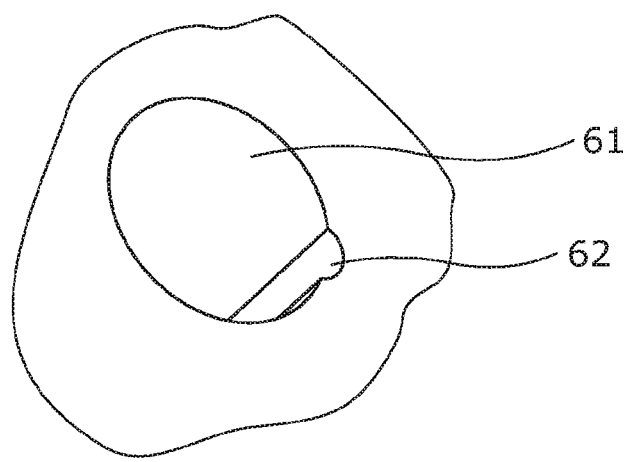
FIG. 8 illustrates the hole in the housing in which the bolt sensor is mounted.
Figure 9:
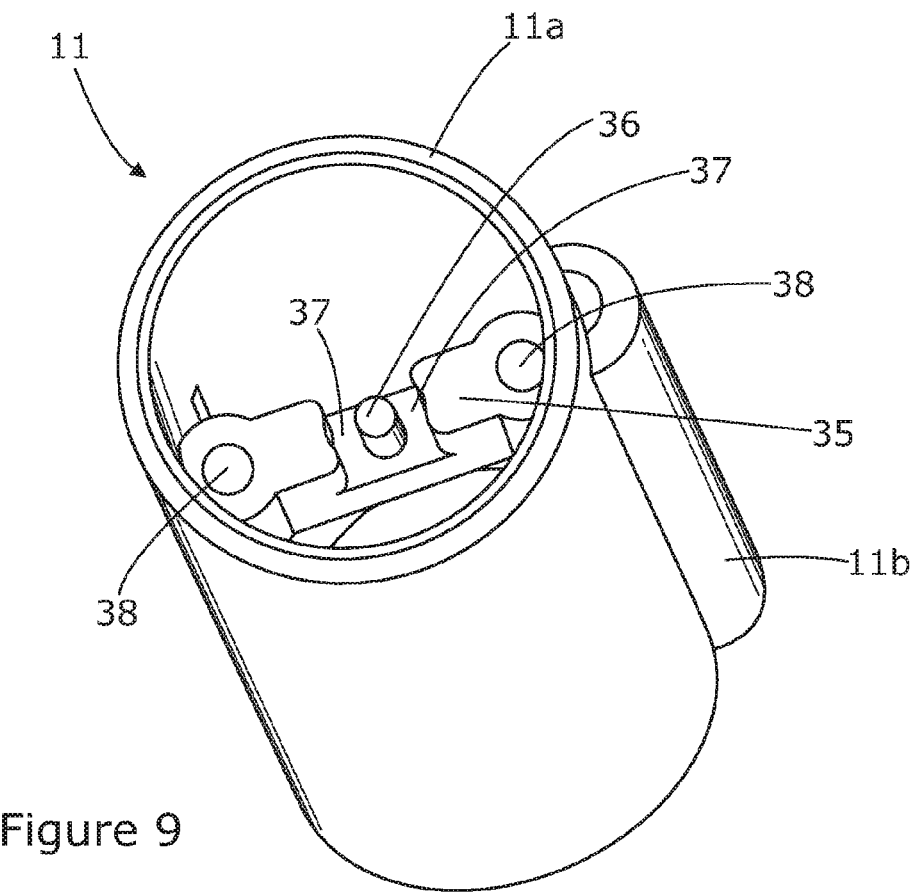
FIG. 9 is a schematic view of the end of a component of the bolt sensor illustrated in FIG. 1.
Figure 9A:
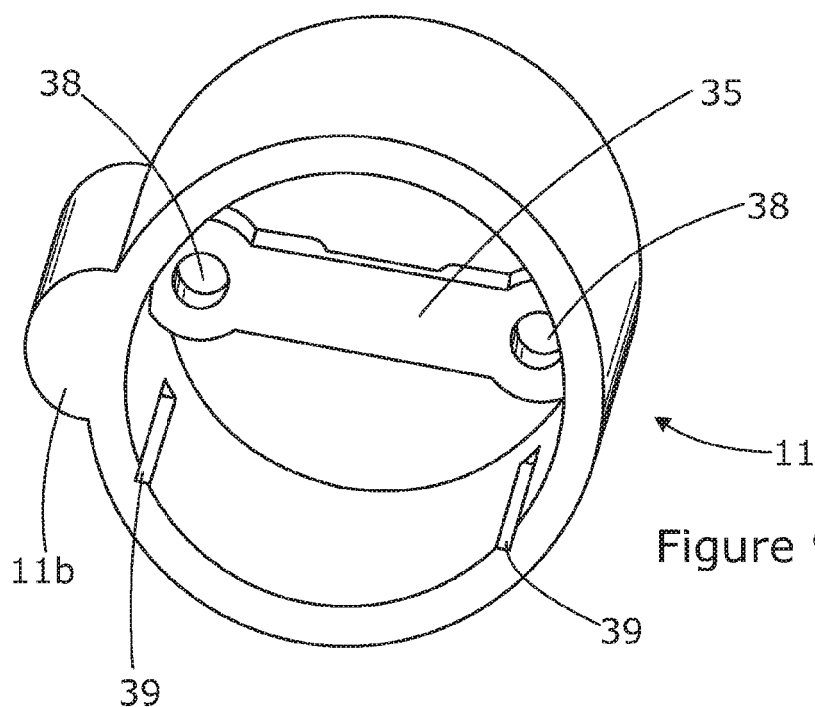
FIG. 9*a* is a schematic cross-sectional top view of the component illustrated in FIG. 9.
Figure 10:
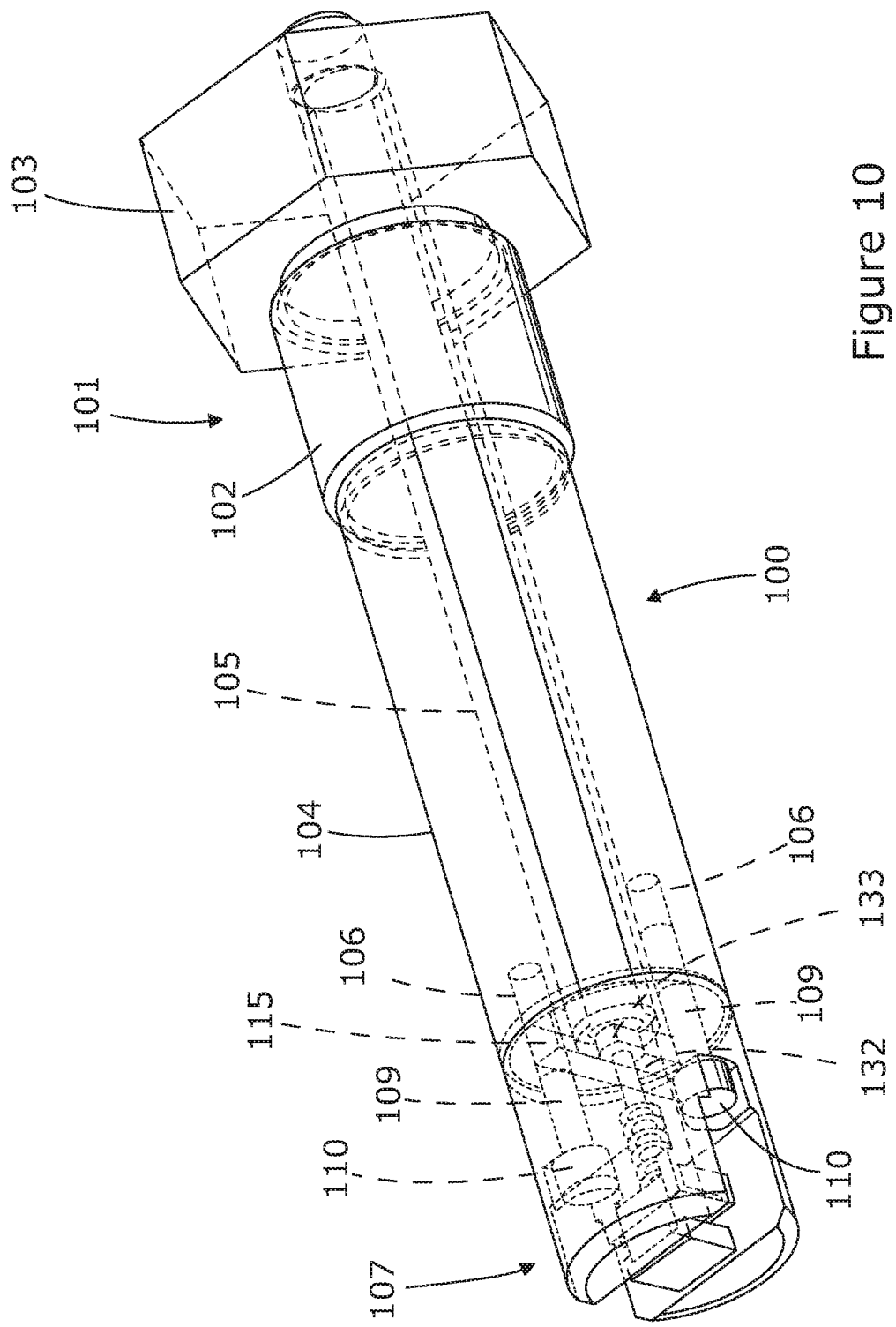
FIG. 10 is a schematic representation of a bolt sensor according to a second embodiment of the invention.
Figure 11:
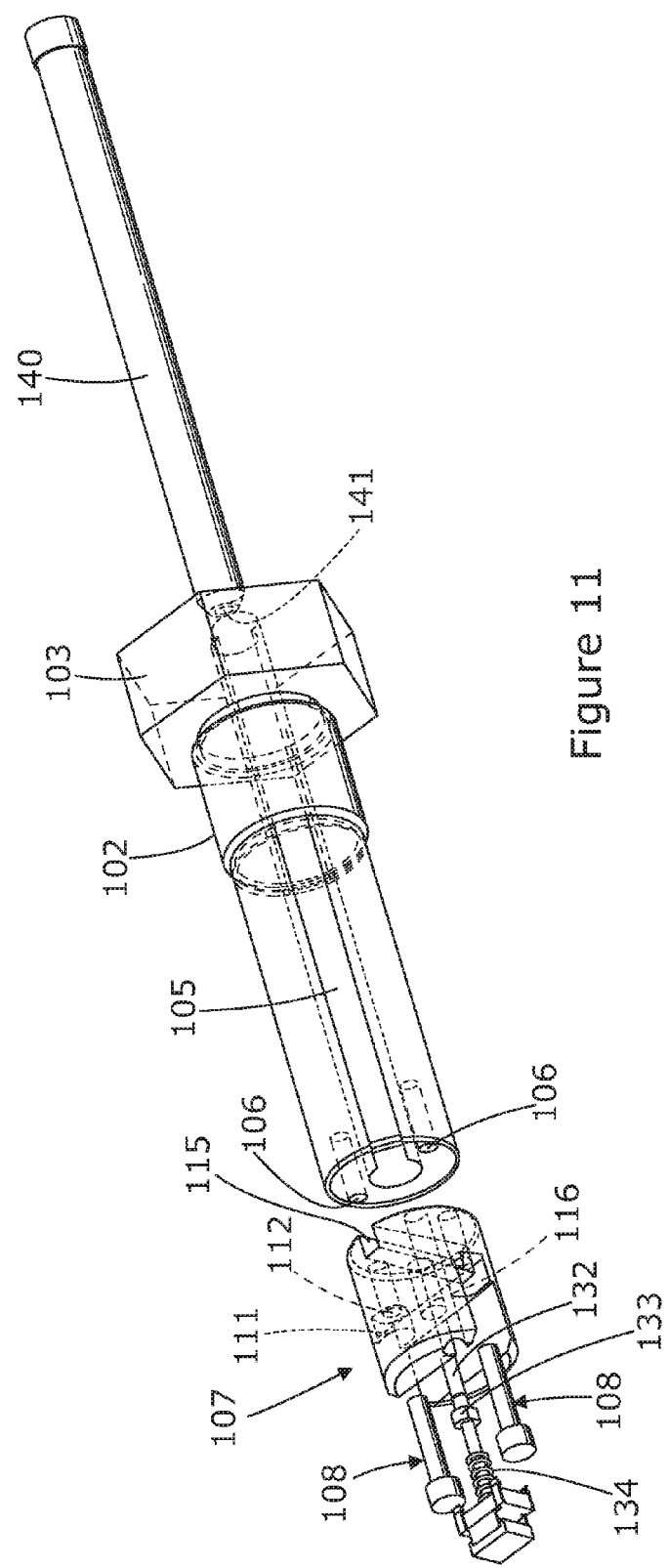
FIG. 11 is an exploded view of the bolt sensor illustrated in FIG. 10.

FIGS. 7 and 8 illustrates a component 60 having a bolt sensor 1 mounted therein. The component 60 includes a bore 61 which has a recess 62 in the wall thereof. The bolt sensor 1 is aligned with the bore 61 such that the rib 11b is aligned with the recess 62.

The friction strain sensor assembly functions as follows:

The springs 27 exert a force urging the base plate 21 out of the hollow portion 11, this movement limited by abutment of the underside of pin heads 26a with the top surface of the bridge 35. The spring 33 pushes the plate 31 away from the bridge 35, which acts as a reaction member, and hence urges the friction strain sensor element 30 out of the aperture 24. The rectangular shape of the aperture 24 and the friction strain sensor element 30 constrain the friction strain sensor element to reciprocal movement in the axial direction of the hollow portion 11.

The spring 33 is specified such that the friction strain sensor element 30 is urged against a surface engaged by the lower surface of the base plate 21 with a pre-determined force on the friction strain sensor element 30 when the bolt sensor 1 is in place.

Hence, when a bolt sensor 1 is introduced into a bore 61, as the bolt head 3 is rotated base plate 21 comes into abutment with a surface of a component adjacent the end of the bore 61, and further rotation of the bolt head causes the base plate 21 to slide into the hollow portion 11, compressing the springs 27 and the seal 50.

As the base plate 21 slides into the hollow portion 21, the friction strain sensor element 30 moves closer to the surface of the component adjacent the end of the bore 61 and is urged against the said surface by the spring 33.

When the bolt sensor is released from the bore 61 the reverse occurs.

The seal 50 prevents ingress of lubricant or contaminants to the region immediately surrounding the friction strain sensor element 30.

The base 21 therefore protects the sensitive sensor element 30, as the sensor element 30 sits behind the surface of the base plate 21, until the base plate 21 engages a surface that is to be instrumented by the sensor element 30.

An antenna 52 is mounted in a collar 51 that sits in the head 3 of the bolt member 2. The antenna 52 is powered by a power connector 53, which includes a cap 54 and a socket 55. The friction strain sensor 30, the AE sensor and the vibration and temperature sensors may communicate with the antenna wirelessly, or may be connected by wires. The antenna 52 may relay information wirelessly.

A second embodiment of the invention is illustrated in FIGS. 10 to 13. In this embodiment, shear forces on the friction strain sensor element are avoided by positioning the friction strain sensor element so that it may be moved to engage the component to be monitored by moving the friction strain sensor element along the axis of the bolt, after the bolt has been positioned in the hole, when the bolt is stationary, thereby avoiding shear forces acting on the friction strain sensor element 30.

The bolt sensor 100 comprises a bolt member 101 including a threaded collar 102 and a hexagonal head 103. A elongate portion 104 extends from and is attached to the end of the collar 102. The elongate portion 104 includes a central bore 105 and two threaded holes 106 situated to either side of the central bore 105 and extending into the free end of the elongate portion 104.

An end cap 107 attaches to the free end of the elongate portion 104 by means of screws 108. The end cap 107 includes screw head seats 111 and holes 112, which are aligned with the holes 106, with a shank 109 of one of the screws 108 passing through a hole 112 and engaging with a hole 106 until the screw's head 110 is seated in the screw head seat 111.

The end of the cap 107 that abuts the end of the elongate portion 104 includes a channel 115 and a bore 116, which aligns with the central bore 105.

A friction strain sensor element assembly 130 includes a mount 131 mounting a friction strain sensor element 131a, and a shaft 132. The shaft 132 includes a collar 133 extending around the shaft 132 and fast with respect to the shaft 132, and a spring 134. The shaft 132 is attached to the friction strain sensor element mount 131 such that the axial movement of the shaft 132 causes axial movement of the mount 131.

The shaft 132 sits in the bore 116, with the collar 133 situated in the channel 115, the flat sides of the collar engaging the parallel walls of the channel 115, thereby preventing rotation of the shaft 132. The bore 116 is smaller in diameter than the spring 134, the spring 134 engaging the wall immediately around the bore 116, thereby urging the mount 131 axially out of end cap 107.

An actuating thumb screw 140 is mounted in the central bore 105. One end 141 of the thumb screw 140 is configured to attach releasably to the shaft 132. The end 141 of the thumb screw includes an internally threaded bore, and the shaft 132 is threaded externally between the free end of the shaft proximate the thumb screw 140 and the collar 133. By rotating the thumb screw 140 the corresponding threads of the shaft 132 and thumb screw 140 cause the shaft 132 and hence the friction strain sensor element assembly 130 to move in the axial direction of the thumb screw 140. Rotating the thumb screw 140 in one direction causes the shaft 132 and hence the mount 131 and frictions sensor element 131a to retract into the channel 135 compressing the spring 134. The mount 131 is most retracted when the collar 133 engages the end 141 of the thumb screw 140.

Rotating the thumb screw 140 in the other direction causes the mount 131 and friction sensor element 131a to move axially in a direction out of the channel 135 so that the friction sensor element 131a engages a component facing the end of the end cap 107.

A hole 150 accommodates a cable that attaches to the friction strain sensor 131a.

Before introducing the bolt sensor 100 into a hole, the thumb screw is rotated to draw the friction strain sensor mount 131 into the channel 135 such that the friction strain sensor element 131a lies behind the end face of the bolt cap 107. The bolt sensor 100 is introduced into a hole and turned until the end of the end cap 107 is in abutment with the surface of a component to be monitored. The thumb screw 140 is then turned in the opposite direction which moves the mount 131 and friction sensor element 131a toward the component to be monitored. The force of the spring 134 pushes the friction strain sensor element 131a into engagement with the surface of the component to be monitored.

Both illustrated embodiments of the invention provide a bolt sensor utilising a friction strain sensor element, which is desirable, and prevent the friction strain sensor element from being subjected to the kind of forces which are likely to damage it.

In both embodiments, the springs urging the friction strain sensor element against the component being monitored ensure that the friction strain sensor element is subjected to the required load for operation of the friction strain sensor element.

Individual technical features of the illustrated embodiments are not limited to use in those embodiments, and may where suitable, be used with any embodiment falling within the scope of the claims.

The invention claimed is:

1. A bolt sensor assembly comprising:
a body configured to be inserted into a hole in a component, the body having a first end and a second end, and a longitudinal axis extending therebetween, wherein
the first end includes an attachment means for attachment of the bolt sensor assembly to the component, wherein
a sensor element is mounted to the second end and wherein the sensor element is movable with respect to the body in the direction of the longitudinal axis of the body and wherein the sensor element is constrained against rotation about the longitudinal axis with respect to the body,
wherein at least a part of the body comprises the second end, the hole, and cooperating elements that prevent relative rotation therebetween, and
wherein sensor element is biased to project from the second end of the body.

2. The bolt sensor assembly according to claim 1, wherein at least a part of the body is rotatable about the longitudinal axis to engage and disengage the body from the hole.

3. The bolt sensor assembly according to claim 2, wherein the body includes a threaded portion for engagement with a correspondingly threaded portion of the hole.

4. The bolt sensor assembly according to claim 1, wherein the sensor element is a temperature sensor.

5. The bolt sensor assembly according to claim 1, wherein the attachment means comprises a collar that is slidably mounted on the body.

6. The bolt sensor assembly according to claim 5, wherein the attachment means is mounted on the body for relative rotation therebetween.

7. The bolt sensor assembly according to claim 5, further comprising a biasing element located between the body and the attachment means, the biasing element configured to urge the body and the attachment means in opposite directions along the longitudinal axis.

8. The bolt sensor assembly according to claim 1, wherein sensor element is provided within a sensor assembly that is mounted at the second end of the body, the assembly comprising a base including an opening in which the sensor element is slidably mounted, a reaction member and a biasing means disposed between the sensor element and the reaction member.

9. The bolt sensor assembly according to claim 8, wherein the sensor assembly further includes a mount to which the sensor element is attached, and wherein the biasing means is disposed between the mount and the reaction member.

10. The bolt sensor assembly according to claim 1, wherein the sensor element is movable between a first position and a second position, in the first position the sensor element is positioned behind the second end of the body and in the second position at least a part of the sensor element is disposed at the second end of the body, the bolt sensor assembly further comprising an actuator adapted to move the sensor element between the first and second positions.

11. The bolt sensor assembly according to claim 10, wherein the body includes a bore and the actuator acts on the sensor element through the bore.

12. The bolt sensor assembly according to claim 11, wherein the sensor element is mounted on a shaft, and the actuator engages the shaft.

13. The bolt sensor assembly according to claim 10, further comprising biasing means arranged to exert a force on the sensor element biasing it into the second position.

14. The bolt sensor assembly according to claim 10, wherein the end of the body in which the sensor element is mounted is configured such that the friction strain sensor element is constrained against rotation with respect to the body about the longitudinal axis.

15. The bolt sensor assembly according to claim 10, wherein the second end of the body comprises a removable cap attachable to the remainder of the body, the sensor element mounted in the cap.

16. The bolt sensor assembly according to claim 1, wherein the sensor element-is an acoustic emission sensor.

17. The bolt sensor assembly according to claim 1, wherein the sensor element is a vibration sensor.

18. The bolt sensor assembly according to claim 1, wherein the sensor element is a strain gauge sensor.

19. The bolt sensor assembly according to claim 1, wherein the sensor element is a friction strain gauge sensor.

* * * * *